United States Patent [19]

Mauck et al.

[11] Patent Number: 4,812,399
[45] Date of Patent: Mar. 14, 1989

[54] ANALYTICAL ELEMENT AND METHOD FOR THE DETERMINATION OF CREATININE OR CREATINE

[75] Inventors: John C. Mauck; Linda A. Mauck; Gary E. Norton, all of Rochester, N.Y.

[73] Assignee: Eastman Kodak Company, Rochester, N.Y.

[21] Appl. No.: 854,460

[22] Filed: Apr. 21, 1986

[51] Int. Cl.$^4$ ............................................. C12Q 1/34
[52] U.S. Cl. ...................................... 435/18; 435/25; 435/28; 435/810
[58] Field of Search ............................. 435/18, 28, 25

[56] References Cited

U.S. PATENT DOCUMENTS

| | | |
|---|---|---|
| 3,806,416 | 4/1974 | Möllering et al. |
| 3,806,420 | 4/1974 | Holz et al. |
| 3,907,644 | 9/1975 | Möllering et al. |
| 4,039,384 | 8/1977 | Luzuki et al. |
| 4,215,197 | 7/1980 | Tarbutton ............................. 435/18 |
| 4,645,739 | 2/1987 | Deeg et al. ............................. 435/18 |

FOREIGN PATENT DOCUMENTS

| | | |
|---|---|---|
| 57-058895 | 4/1982 | Japan. |
| 57-083297 | 5/1982 | Japan. |
| 58-009699 | 1/1983 | Japan. |
| 58-016674 | 1/1983 | Japan. |

OTHER PUBLICATIONS

Rochi et al., *Biochem. Biophys. Acta* 6, pp. 210–216 (1950).
Tsuru et al., *Agr. Biol. Chem.* 40 (5), pp. 1011–1018 (1976).
Torelli—Chem. Abst., vol. 98 (1983) p. 103,926j.
Toyobo—Chem. Abst., vol. 97 (1982) p. 123,449p.
Asano et al.—Chem. Abst., vol. 103 (1985) p. 175,004b.

*Primary Examiner*—Sam Rosen
*Attorney, Agent, or Firm*—J. Lanny Tucker

[57] ABSTRACT

An analytical element can be used for the determination of either creatinine or creatine or both. The element contains creatinine amidohydrolase, creatine amidinohydrolase and sarcosine oxidase, and a leuco dye which is capable of providing a detectable dye in the presence of hydrogen peroxide and a peroxidative substance. The creatine amidinohydrolase is present in a manner such that it is substantially inert to the leuco dye. The creatinine amidohydrolase is present in a rate limiting amount. By measuring the amount of dye formation at particular times during the assay, either or both of the analytes can be determined with the same element.

20 Claims, 2 Drawing Sheets

ANALYTICAL ELEMENT AND METHOD FOR THE DETERMINATION OF CREATININE OR CREATINE

FIELD OF THE INVENTION

The present invention relates to clinical chemistry. In particular, it relates to an analytical element and method for the determination of either creatinine or creatine in aqueous liquids, e.g. biological fluids.

BACKGROUND OF THE INVENTION

The determination of the intermediate and end products of protein metabolism is important in clinical chemistry, and particularly in the diagnosis of kidney function. The products of this metabolism include creatinine and creatine.

Creatinine is a product of the endogenous metabolism of muscle. The amount of creatinine in the urine reflects total muscle mass and the degree of muscle activity. The amount of creatinine in a person's urine is generally constant, varying little from day to day.

Urinary creatine is elevated in the early stages of muscular dystrophy, when muscle destruction is occurring rapidly, and in any wasting disease involving increased tissue catabolism. It is elevated during severe and strenuous muscular activity and in hyperthyroidism. Urinary creatinine is decreased during the later stages of muscular dystrophy and whenever renal function is impaired. Urinary creatine increases in the same disease states that produce an increase in urinary creatinine.

Methods for the determination of creatinine have been frequently described. Early tests were based on the nonenzymatic Jaffe reaction which involves the formation of an orange-red color with an alkaline picrate solution. This method, however, is not specific for creatinine since many creatinine-like substances also react with alkaline picrate.

Enzymatic assays for creatinine have been developed using enzymes specific for creatinine and creatine, respectively, and the following reaction sequence:

(1)

(2)

The first reaction is catalyzed by creatinine amidohydrolase whereas the second one is catalyzed by creatine amidinohydrolase.

An assay for creatinine is described in U.S. Pat. No. 4,215,197 (issued July 29, 1980) wherein the enzymes noted above are used in combination with a tetrazolium indicator. The assay can be performed in solution or with a dry device into which the reagents have been imbibed. Only creatinine can be measured when all of the reagents are included in the analytical composition. As shown in Example I (Col. 5, line 64 to Col. 6, line 24) of this reference, the assay requires a long incubation period (i.e. up to sixty minutes), and a blanking step to subtract out background resulting from the reagents used and endogenous creatine. The sensitivity is allegedly increased by including formaldehyde dehydrogenase, diaphorase and NAD in the composition. This significantly complicates the assay with additional reagents and enzymatic reactions. Creatine or sarcosine can be measured with the assay if the appropriate enzymes are omitted. But this requires separate compositions or test devices for determining each analyte.

Japanese Patent Publication 58(1983)-009699 (published Jan. 20, 1983) describes an apparatus and method for solution assay of either creatinine or creatine. The assay is quite complex, requiring extensive reaction chambers, fluid pumps and multiple signal detecting equipment. Two readings are taken to determine both analytes. However, the assay does not measure the amount of creatinine independently, but rather as the difference between two end point measurements.

It would be desirable to have a relatively simple, automated dry assay that is equally useful for either creatinine or creatine determination, which is highly sensitive and rapid and requires no blanking step.

SUMMARY OF THE INVENTION

The problems encountered with known assays are overcome with an analytical element comprising an absorbent carrier material containing creatinine amidohydrolase, creatine amidinohydrolase and sarcosine oxidase, and a leuco dye which is capable of providing a detectable dye in the presence of hydrogen peroxide and a peroxidative substance, the creatine amidinohydrolase being present in a manner such that it is substantially inert to the imidazole leuco dye, and the creatinine amidohydrolase being present in a rate limiting amount.

In a preferred embodiment, a multilayer analytical element for the determination of either creatinine or creatine comprises a support having thereon, in order, a first reagent layer containing sarcosine oxidase, a rate limiting amount of creatinine amidohydrolase, a peroxidative substance and an imidazole leuco dye which is capable of providing a detectable dye in the presence of the peroxidative substance and hydrogen peroxide, a second reagent layer containing creatine amidinohydrolase, and a porous spreading layer.

A method for the determination of either creatinine or creatine comprises the steps of:

A. in the presence of a peroxidative substance, contacting a sample of a liquid suspected of containing either creatinine or creatine with an analytical element comprising an absorbent carrier material containing creatinine amidohydrolase, creatine amidinohydrolase and sarcosine oxidase, and a leuco dye which is capable of providing a detectable dye in the presence of hydrogen peroxide and the peroxidative substance, the creatine amidinohydrolase being present in a manner such that it is substantially inert to the leuco dye, and the creatinine amidohydrolase being present in a rate limiting amount, and B. determining the detectable dye formed as a result of the presence of either creatinine or creatine.

The present invention provides a relatively simple, automated means to rapidly and economically measure either creatinine or creatine or both with the same analytical element. Separate analytical compositions or elements are therefore not needed for the different analytes. The assay of this invention is rapid, allowing measurement of either analyte within, for example, about 5 minutes. It is also possible to avoid tedious blanking steps with the present invention. The complex equipment used for solution assays described in Japanese Patent Publication 58(1983)-009699 is therefore avoided with the present invention.

These advantages are possible with the present invention because it is a kinetic assay for creatinine performed with the analytical element described herein. This element contains creatinine amidohydrolase and creatine amidinohydrolase which promote the two enzymatic reactions (1) and (2) noted above. However, the creatinine amidohydrolase is present in a rate limiting amount so that once endogenous creatine has completely reacted, the rate of dye formation is due totally to the presence of creatinine. However, creatine can also be accurately measured with this element by measuring the amount of dye formation early in the assay. Background is minimized by putting the reagents into the element in such a manner that they do not interfere with each other. In particular, the creatine amidinohydrolase is present in a manner such that it is substantially inert to the leuco dye.

DETAILED DESCRIPTION OF THE INVENTION

Figure 1:
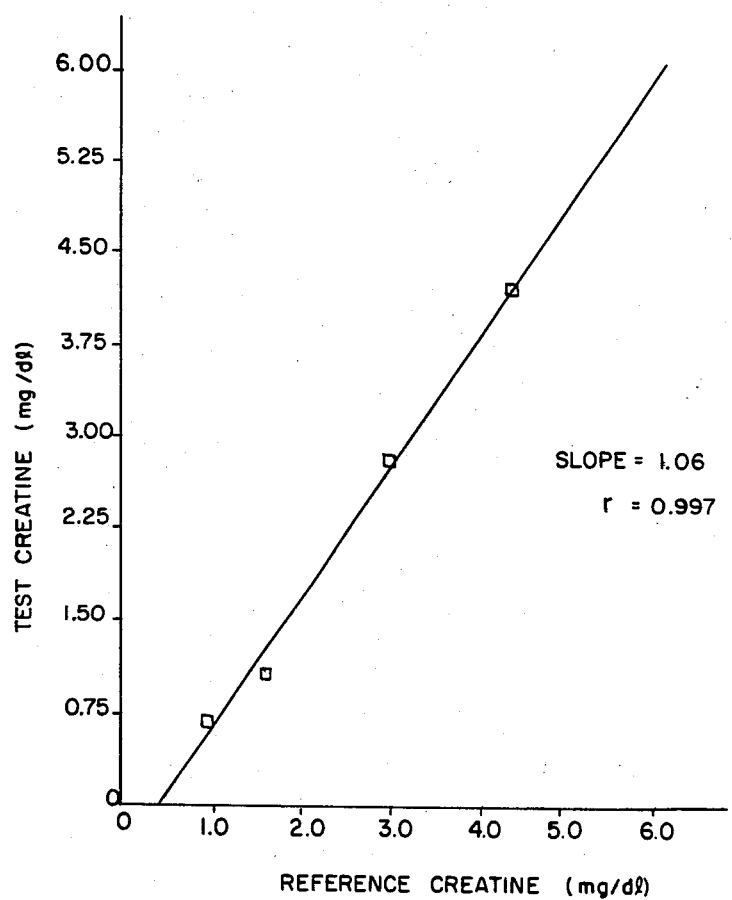
FIG. 1 is a graphical plot of creatine determined by a reference method vs. creatine determined by the method of this invention.

The present invention relates to the determination (qualitative or quantitative measurement) of either creatinine or creatine in aqueous liquids. In particular, the invention can be used to assay biological fluids of animals and humans. Such fluids include, but are not limited to, whole blood, plasma, sera, lymph, bile, urine, spinal fluid, sputum, perspiration and the like as well as stool secretions. It is also possible to assay fluid preparations of human or animal tissue such as skeletal muscle, heart, kidney, lungs, brains, bone marrow, skin and the like. Preferably, human serum or urine is assayed with this invention.

The method of this invention is practiced using a dry analytical element. The simplest element can be composed of an absorbent carrier material, e.g. a thin sheet of a self-supporting absorbent or bibulous material, such as filter paper or strips, which contains the reagents needed for the assay. The element can be divided into two or more discrete zones with different reagents incorporated into individual zones of the carrier material. Such elements are known in the art as test strips, diagnostic elements, dip sticks, diagnostic agents and the like.

Useful absorbent carrier materials are insoluble and maintain their structural integrity when exposed to water or biological fluids such as urine or serum. Useful elements can be prepared from paper, porous particulate structures, porous polymeric films, cellulose, glass fibers, woven and nonwoven fabrics (synthetic and nonsynthetic) and the like. Useful materials and procedures for making such elements are well known in the art.

Preferably, the dry analytical element of this invention has a porous spreading zone. This zone can be self-supporting (i.e. composed of a material rigid enough to maintain its integrity), but preferably it is carried on a separate nonporous support. Such a support can be any suitable dimensionally stable, and preferably, nonporous and transparent (i.e. radiation transmissive) material which transmits electromagnetic radiation of a wavelength between about 200 and about 900 nm. A support of choice for a particular element should be compatible with the intended mode of detection (transmission or reflectance spectroscopy). Useful supports can be prepared from paper, metal foils, polystyrene, polyesters [e.g. poly(ethylene terephthalate)], polycarbonates, cellulose esters (e.g. cellulose acetate), etc.

The porous spreading zone can be prepared from any suitable fibrous or non-fibrous material or mixtures of either or both as described in U.S. Pat. Nos. 4,292,272 (issued Sept. 29, 1981 to Kitajima et al), 3,992,158 (issued Nov. 16, 1976 to Przybylowicz et al), 4,258,001 (issued Mar. 24, 1981 to Pierce et al) and 4,430,436 (issued Feb. 7, 1984 to Koyama et al) and Japanese Patent Publication 57(1982)-101760 (published June 24, 1982). It is desirable that the spreading zone be isotropically porous, meaning that the porosity is the same in each direction in the zone as caused by interconnected spaces or pores between particles, fibers, polymeric strands, etc.

The elements can have two or more discrete zones, either in the same layer or superimposed, at least one of which is preferably a porous spreading zone. The other zones can be reagent zones or registration zones as those zones are known in the art, additional spreading zones, radiation-blocking or filter zones, subbing zones, barrier zones, etc. The zones are generally in fluid contact with each other, meaning that generally fluids, reagents and reaction products (e.g. color dyes) can pass or be transported between superposed regions of adjacent zones. Preferably, the zones are separately coated and superposed layers.

The assay of this invention is accomplished with the following sequence of reactions (1)–(4):

creatinine + water ⇌ creatine    (1)

creatine + water → urea + sarcosine    (2)

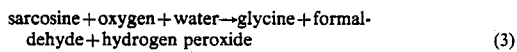
sarcosine + oxygen + water → glycine + formaldehyde + hydrogen peroxide    (3)

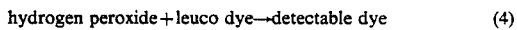
hydrogen peroxide + leuco dye → detectable dye    (4)

These reactions are catalyzed by creatinine amidohydrolase, creatine amidinohydrolase, sarcosine oxidase and a peroxidative substance, respectfully.

The enzymes described herein can be used in the practice of this invention in pure form, as fermentation solutions or as impure extracts of the enzymes, individually or collectively.

Creatinine amidohydrolase and creatine amidinohydrolase can be obtained commercially from a number of sources. Several species of each enzyme, isolated from various microbial sources, are described in U.S. Pat. Nos. 3,806,416 (issued Apr. 23, 1974 to Mollering et al) and 4,039,384 (issued Aug. 2, 1977 to Suzuki et al). Any of the species can be used in the practice of this invention. The creatinine amidohydrolase having a pH optimum of 6.5 at 37° C. and the creatine amidinohydrolase having a pH optimum of 7.7 at 37° C., both obtained from a strain of Flavobacterium and described in U.S. Pat. No. 4,039,384, are preferred.

Sarcosine oxidase can also be obtained commercially from a number of sources. This enzyme is described, for example, in U.S. Pat. No. 4,216,292 (issued Aug. 5, 1980 to Ikuta et al) and Jap. Patent Publications 56(1981)-092,790 (published July 27, 1981) and 57(1982)-036,985 (published Feb. 27, 1982). Sarcosine oxidase from any source is useful in the practice of this invention Peroxidative substances useful in this invention include peroxidase. A peroxidase is an enzyme which will catalyze a reaction wherein hydrogen peroxide oxidizes another substance. The peroxidases are generally conjugated proteins containing iron porphyrin. Peroxidase occurs in horseradish, potatoes, fig tree sap and turnips, milk and white blood cells. It also occurs in microorganisms and can be produced by fermentation. Certain synthetic peroxidases are also known. Peroxidase is a preferred peroxidative substance, but other substances which are not enzymes are also useful. Many of these are commercially available.

The leuco dyes useful in this invention are imidazole leuco dyes which are generally colorless in the leuco form, but which can be oxidized to a detectable colored dye in the presence of hydrogen peroxide and a peroxidative substance. Useful leuco dyes include di- and triarylimidazoles such as those described in U.S. Pat. No. 4,089,747 (issued May 16, 1978 to Bruschi), E.P. Application 122,641 (published Oct. 24, 1984) and Jap. Patent Publication 58(1983)-045,557 (published Mar. 16, 1983). Particularly useful imidazole leuco dyes are the triarylimidazoles described in U.S. Pat. No. 4,089,747, including, e.g. 2-(3,5-dimethoxy-4-hydroxyphenyl)-4,5-bis(4-dimethyl-aminophenyl)imidazole, 2-(4-hydroxy-3-methoxyphenyl)-4,5-bi(p-dimethylaminophenyl)-1H-imidazole, 2-(3-ethoxy-4-hydroxyphenyl-4,5-bis(p-dimethylaminophenyl)-1H-imidazole, 2-(4-hydroxy-3,5-dimethoxyphenyl)-4-[4-(dimethylamino)phenyl]-5-(2-furyl)imidazole, 2-(4-hydroxy-3,5-dimethoxyphenyl)-4,5-di(2-furyl)imidazole, 2-(3,5-dimethoxy-4-hydoxyphenyl)-4-[4-(dimethylamino)phenyl]-5-phenethylimidazole and 2-(3,5-dimethoxy-4-hydroxyphenyl)-4-[4-(dimethylamino)phenyl]-5-benzylimidazole.

The elements of this invention can also contain one or more other addenda commonly included in the elements for various manufacturing or operational advantages. Such addenda include surfactants, ion chelating agents, buffers, solvents, hardeners, antioxidants, coupler solvents, and the like.

It is critical that the creatinine amidohydrolase be present in the element in a rate limiting amount. This means that the amount of this enzyme in relation to the amount of creatine amidinohydrolase is such that the forward direction of reaction (1) noted above is rate controlling. The specific amount of creatinine amidohydrolase can be readily determined by a skilled clinical chemist. Generally, the amount is less than about 2500, and preferably from about 100 to about 1000, I.U./m². Creatine amidinohydrolase can be present in any amount as long as it is not a rate limiting amount. In other words, reaction (2), noted above, is not to be controlling in the assay. The specific amount of this enzyme can be readily determined by a skilled clinical chemist.

Another way of stating the amounts of creatine amidinohydrolase and creatinine amidohydrolase is that they are generally present in a coverage ratio of activity (I.U. per m²) of at least about 50:1. Preferably, this ratio is at least about 100:1.

As used in the context of this disclosure and the claims, I.U. represents the International Unit for enzyme activity defined as one I.U. being the amount of enzyme activity required to catalyze the conversion of 1 micromole of substrate per minute under standard pH and temperature conditions for the enzyme. For the preferred enzyme preparations used in this invention, these standard conditions are 37° C. and pH 7.5 for creatinine amidohydrolase, 37° C. and pH 7.5 for creatine amidinohydrolase, 37° C. and pH 7.5 for sarcosine oxidase and 37° C. and pH 7.5 for peroxidase.

The other reagents useful in the assay are present in suitable amounts readily determined by a skilled clinical chemist. Representative amounts are illustrated in the examples below.

It is critical in the practice of this invention that the creatine amidinohydrolase and leuco dye are present in a manner such that the enzyme is substantially inert to the dye. This means that the two reagents are incorporated in the element in such a manner that the enzyme does not adversely affect the leuco dye. This can be accomplished in a number of ways. For example, the enzyme can be used in a highly pure form so that the leuco dye is not affected by any impurities. More practically, however, the enzyme cannot be obtained in a highly pure form. In such cases, either or both the enzyme and dye can be encapsulated or otherwise isolated from each other in the element until the assay is carried out. Preferably, the enzyme and leuco dye are located in different zones or layers of the element so that they do not mix until the time of the assay.

A variety of different elements, depending on the method of assay, can be prepared in accordance with the present invention. Elements can be configured in a variety of forms, including elongated tapes of any desired width, sheets, slides or chips.

The assay of this invention can be manual or automated. In general, in using the dry elements, creatinine or creatine determination is made by taking the element from a supply roll, chip packet or other source and physically contacting it with a sample (e.g. 1 to 200 μl) of the liquid to be tested so that the sample and reagents within the element become mixed. Such contact can be accomplished in any suitable manner, e.g. dipping or immersing the element into the sample or, preferably, by spotting the element by hand or machine with a drop of the sample with a suitable dispensing means.

After sample application, the element is exposed to any conditioning, such as incubation, heating or the like, that may be desirable to quicken or otherwise facilitate obtaining any test result.

The rate of dye formation is then measured with suitable reflection or transmission spectrophotometric equipment and procedures. Generally, for creatine determination, a dye measurement is made prior to substantial conversion of creatinine, i.e. soon after sample-element contact, e.g. prior to about 1 minute after sample-element contact. This measurement determines endogenous creatine because the rate limiting amount of creatinine amidohydrolase in the element has converted substantially no creatinine to creatine at this point.

For creatinine determination, at least two dye measurements are made after substantially all endogenous creatine has been converted enzymatically to reaction products. Generally, the first measurement is made at least about 4 minutes after sample-element contact. Another measurement is made thereafter in order to determine the rate of dye formation, and hence, the amount of creatinine. This sequence of measurements allows the use of the present element to measure either or both creatinine and creatine.

In the examples which follow, illustrating the practice of this invention, the materials used were obtained as follows:

TRITON X-100 and X-405 surfactants from Rohm and Haas (Philadelphia, Pa., U.S.A.), BRIJ 78 surfactant from ICI Americas (Wilmington, Del., U.S.A.), ESTANE polyurethane resin from B. F. Goodrich (Cleveland, Ohio, U.S.A.), ALKANOL XC surfactant from DuPont (Wilmington, Del., U.S.A.), creatinine amidohydrolase, creatine amidinohydrolase and sarcosine oxidase from Seishin Pharmaceutical (Japan), peroxidase from Miles Laboratories (Elkhart, Ind., U.S.A.)

N-tris-(hydroxymethyl)methyl-2-aminomethane sulfonic acid buffer from Sigma Chemicals (St. Louis, Mo., U.S.A.), and the remainder either from Eastman Kodak Company (Rochester, N.Y., U.S.A.) or prepared using standard procedures and readily available starting materials.

EXAMPLE 1

Assays for Creatine and Creatinine

This example illustrates the practice of this invention for the determination of creatinine. This assay was carried out with the element having the following components:

| | | |
|---|---|---|
| Spreading Layer | Titanium dioxide | 20–80 g/m$^2$ |
| | Cellulose acetate | 2–10 g/m$^2$ |
| | BRIJ 78 surfactant | 0.3–1.5 g/m$^2$ |
| | TRITON X-405 surfactant | 0.5–5 g/m$^2$ |
| | ESTANE resin | 1–5 g/m$^2$ |
| Subbing Layer | Poly(N—isopropylacrylamide) | 0.1–1 g/m$^2$ |
| Reagent Layer | Gelatin | 1–20 g/m$^2$ |
| | N—tris-(hydroxymethyl)-methyl-2-aminomethane sulfonic acid buffer | 0.5–5 g/m$^2$ |
| | (Ethylenedinitrilo)tetraacetic acid | 0.1–1 g/m$^2$ |
| | Creatine amidinohydrolase | 5,000–50,000 I.U./m$^2$ |
| | Ascorbic acid oxidase | 1,000–10,000 I.U./m$^2$ |
| | TRITON X-100 surfactant | 0.1–2.5 g/m$^2$ |
| Registration/Reagent Layer | Gelatin (hardened) | 1–20 g/m$^2$ |
| | Sarcosine oxidase | 500–10,000 I.U./m$^2$ |
| | Peroxidase | 500–80,000 I.U./m$^2$ |
| | 5,5-dimethyl-1,3-cyclohexanedione | 0.01–1 g/m$^2$ |
| | 2,4-di-n-pentyl phenol | 0.5–5 g/m$^2$ |
| | Creatinine amidohydrolase | 50–2,500 I.U./m$^2$ |
| | N—tris-(hydroxymethyl)-methyl-2-aminomethane sulfonic acid buffer | 0.5–5 g/m$^2$ |
| | (Ethylenedinitrilo)tetraacetic acid | 0.1–1 g/m$^2$ |
| | TRITON X-100 surfactant | 0.1–2.5 g/m$^2$ |
| | ALKANOL XC surfactant | 0.1–2.5 g/m$^2$ |
| | 2,4-di-n-pentyl phenol | 1–5 g/m$^2$ |
| | 5,5-dimethyl-1,3-cyclohexanedione | 0.01–1 g/m$^2$ |
| | 2-(3,5-dimethoxy-4-hydroxyphenyl)-4,5-bis(4-methylaminophenyl)imidazole | 0.1–1 g/m$^2$ |
| /// | Poly(ethylene terephthalate) Support | //// |

This element was used to simultaneously determine creatine and creatinine in the following manner. Separate calibration curves were prepared for creatine and creatinine by applying 10 μl samples of the appropriate calibrator fluids to separate elements, incubating and measuring the resulting dye at 670 nm. Reflectance density ($D_R$) readings were made at 60, 236 and 309 seconds after addition of each sample. The readings made at 60 seconds were used to plot a calibration curve for creatine. This curve enables one to determine creatine in a test sample when the dye measurement is made early in the assay. A calibration curve for creatinine was similarly obtained by subtracting the reading at 236 seconds from the respective reading taken at 309 seconds and dividing by 1.217 for each calibrator sample. This curve enables one to determine the kinetic rate of reaction for creatinine.

Figure 2:
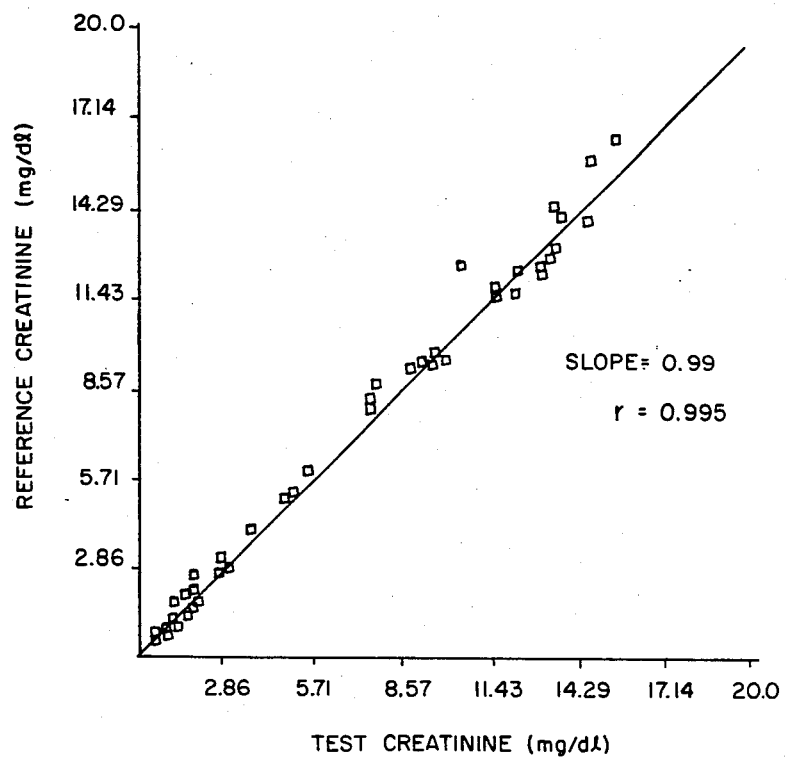
FIG. 2 is a graphical plot of creatinine determined by a reference method vs. creatinine determined by the method of this invention.

Creatine and creatinine were then measured in test samples containing unknown amounts of these analytes by applying a sample of the test fluid to an element of this invention, reading the reflectance densities at the appropriate times and determining the respective analyte concentration from the appropriate calibration curve. FIG. 1 shows a plot of creatine values determined according to this invention vs. creatine values determined with a reference method. FIG. 2 is a plot of creatinine values for a number of test samples determined according to this invention vs. the creatinine values determined according to a reference method.

These FIGS. show that the element of the present invention can be used to rapidly and accurately measure either creatinine or creatine or both.

The invention has been described in detail with particular reference to preferred embodiments thereof, but it will be understood that variations and modifications can be effected within the spirit and scope of the invention.

We claim:

1. An analytical element for the determination of either creatinine or creatine comprising an absorbent carrier material containing creatinine amidohydrolase, creatine amidinohydrolase, sarcosine oxidase and a leuco dye which is capable of providing a detectable dye in the presence of hydrogen peroxide and a peroxidative substance, either or both of said creatine amidinohydrolase and leuco dye being present in encapsulated form or, both being physically isolated from each other until an assay for creatinine or creatine is carried out, and said creatinine amidohydrolase being present in a rate limiting amount.

2. The element of claim 1 wherein said creatine amidinohydrolase and leuco dye are physically located in separate zones of said element.

3. The element of claim 1 wherein said creatine amidinohydrolase and creatinine amidohydrolase are present in an activity coverage ratio of at least about 50:1.

4. The element of claim 1 wherein said leuco dye is a triarylimidazole leuco dye.

5. The element of claim 1 further comprising a peroxidative substance.

6. A multilayer analytical element for the determination of either creatinine or creatine comprising a support having thereon, in order, a first reagent layer containing sarcosine oxidase, a rate limiting amount of creatinine amidohydrolase, a peroxidative substance and an imidazole leuco dye which is capable of providing a detectable dye in the presence of said peroxidative substance and hydrogen peroxide, a second reagent layer containing creatine amidinohydrolase, and a porous spreading layer.

7. The element of claim 6 wherein the activity coverage ratio of creatine amidinohydrolase and creatinine amidohydrolase is at least about 50:1.

8. The element of claim 6 wherein said imidazole dye is a triarylimidazole leuco dye.

9. The element of claim 6 wherein said peroxidative substance is peroxidase.

10. A method for the determination of either creatinine or creatine comprising the steps of:

A. in the presence of a peroxidative substance, contacting a sample of a liquid suspected of containing either creatinine or creatine with an analytical element comprising an absorbent carrier material containing creatinine amidohydrolase, creatine amidinohydrolase, sarcosine oxidase and a leuco dye which is capable of providing a detectable dye in the presence of hydrogen peroxide and a peroxidative substance, either or both of said creatine amidinohydrolase and leuco dye being present in encapsulated form or, both being physically isolated from each other until an assay for creatinine or creatine is carried out, and said creatinine amidohydrolase being present in a rate limiting amount, and B. determining the detectable dye formed as a result of the presence of either creatinine or creatine.

11. The method of claim 10 for the kinetic determination of creatinine wherein said detectable dye is measured at least twice after substantially all endogenous creatine has been converted to reaction products after said contacting step.

12. The method of claim 10 for the determination of creatine wherein said detectable dye is measured prior to substantial conversion of endogenous creatinine after said contacting step.

13. The method of claim 10 wherein said element further comprises said peroxidative substance.

14. The method of claim 10 wherein said creatine amidinohydrolase and leuco dye are physically located in separate zones of said element.

15. The method of claim 10 wherein said element is a multilayer analytical element comprising a support having thereon, in order, a first reagent layer containing said sarcosine oxidase, a rate limiting amount of said creatinine amidohydrolase, a peroxidative substance and an imidazole leuco dye which is capable of providing a detectable dye in the presence of said peroxidative substance and hydrogen peroxide, a second reagent layer containing said creatine amidinohydrolase, and a porous spreading layer.

16. The method of claim 15 wherein the activity coverage ratio of creatine amidinohydrolase and creatinine amidohydrolase in said element is at least about 50:1.

17. The method of claim 16 wherein the activity coverage ratio is at least about 100:1.

18. The method of claim 15 wherein said imidazole dye is a triarylimidazole leuco dye.

19. The method of claim 10 wherein said peroxidative substance is peroxidase.

20. The method of claim 10 wherein said liquid is human serum or urine.

* * * * *